US00PP31172P2

(12) United States Plant Patent
Hanes

(10) Patent No.: US PP31,172 P2
(45) Date of Patent: Dec. 3, 2019

(54) ***PELARGONIUM* PLANT NAMED 'PEQZ0046'**

(50) Latin Name: ***Pelargonium* interspecific**
Varietal Denomination: PEQZ0046

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,699

(22) Filed: Apr. 10, 2018

(51) Int. Cl.
*A01H 5/02* (2018.01)
*A01H 6/42* (2018.01)

(52) U.S. Cl.
USPC ..... Plt./329
CPC ..... *A01H 6/425* (2018.05)

(58) Field of Classification Search
USPC ..... Plt./329
CPC ..... A01H 6/425
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0046' has intense hot rose colored inflorescences held above the medium dark green foliage that carries a deep zonation, is very heat and drought tolerant with continuous color through the most extreme summer heat, and exceptional edema tolerance on a well-branched plant habit.

1 Drawing Sheet

Latin name of the genus and species of the plant claimed: *Pelargonium* interspecific.
Varietal denomination: 'PEQZ0046'.

BACKGROUND OF THE NEW PLANT

The present invention comprises a new *Pelargonium*, botanically known as *Pelargonium* interspecific, and hereinafter referred to by the variety name 'PEQZ0046'.

'PEQZ0046' is a product of a planned breeding program. The new cultivar 'PEQZ0046' has intense hot rose colored inflorescences held above the medium dark green foliage that carries a deep zonation, is very heat and drought tolerant with continuous color through the most extreme summer heat, and exceptional edema tolerance on a well-branched plant habit.

'PEQZ0046' originates from a hybridization in a controlled breeding program made in August, in a greenhouse in Guatemala. The female parent was an unpatented, proprietary plant of P. interspecific parentage, identified as '11101-1' with violet color florets and smaller more open plant habit when compared to 'PEQZ0046'.

The male parent of 'PEQZ0046' was an unpatented, proprietary plant of P. interspecific parentage, identified as '10984-1' with hot pink florets and a darkly zoned leaf on a less vigorous, smaller plant than 'PEQZ0046'. The resultant seed was sown in February 2012.

'PEQZ0046' was selected as one flowering plant within the progeny of the stated cross in May 2012 in a greenhouse in Gilroy, Calif.

The first act of asexual reproduction of 'PEQZ0046' was accomplished when vegetative stem tip cuttings were propagated from the initial selection in June 2012 in a greenhouse in Gilroy, Calif.

BRIEF SUMMARY OF INVENTION

Horticultural examination of plants grown from cuttings of the plant initiated in June 2012 in Gilroy, Calif., and continuing thereafter, has demonstrated that the combination of characteristics as herein disclosed for 'PEQZ0046' are firmly fixed and are retained through successive generations of asexual reproduction.

'PEQZ0046' has not been observed under all possible environmental conditions. The phenotype may vary significantly with variations in environment such as temperature, light intensity, and day length.

A Plant Breeder's Right for this cultivar has not been applied for. 'PEQZ0046' has not been made publicly available prior to the effective filing date of this application, notwithstanding any disclosure that may have been made less than one year prior to the effective filing date of this application by the inventor or another who obtained 'PEQZ0046' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0046' with colors being as true as possible with an illustration of this type.

Figure 1:
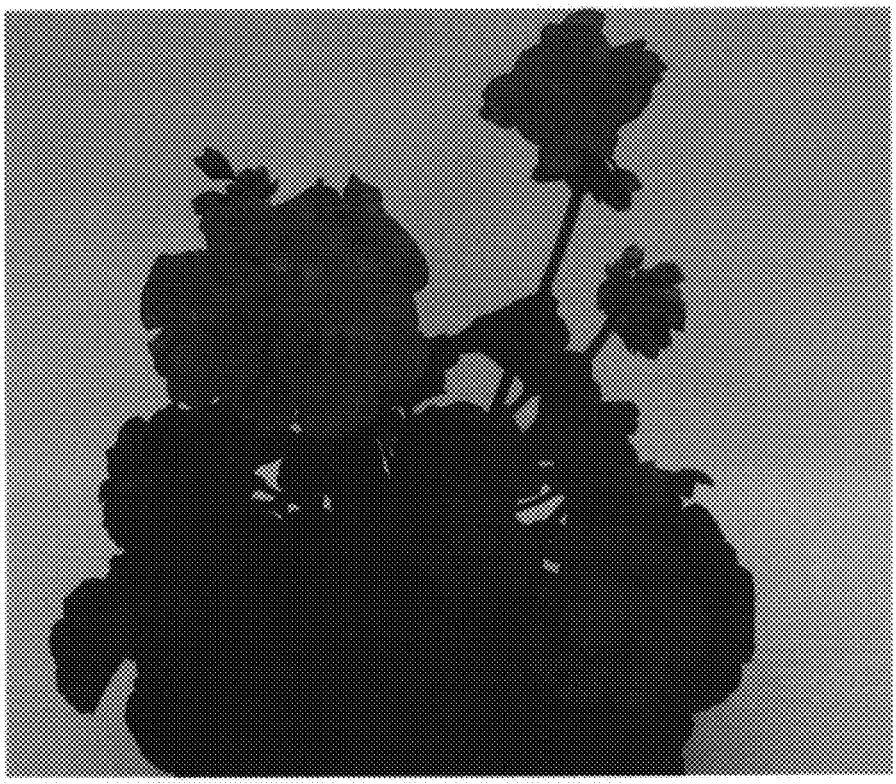
Figure 2:
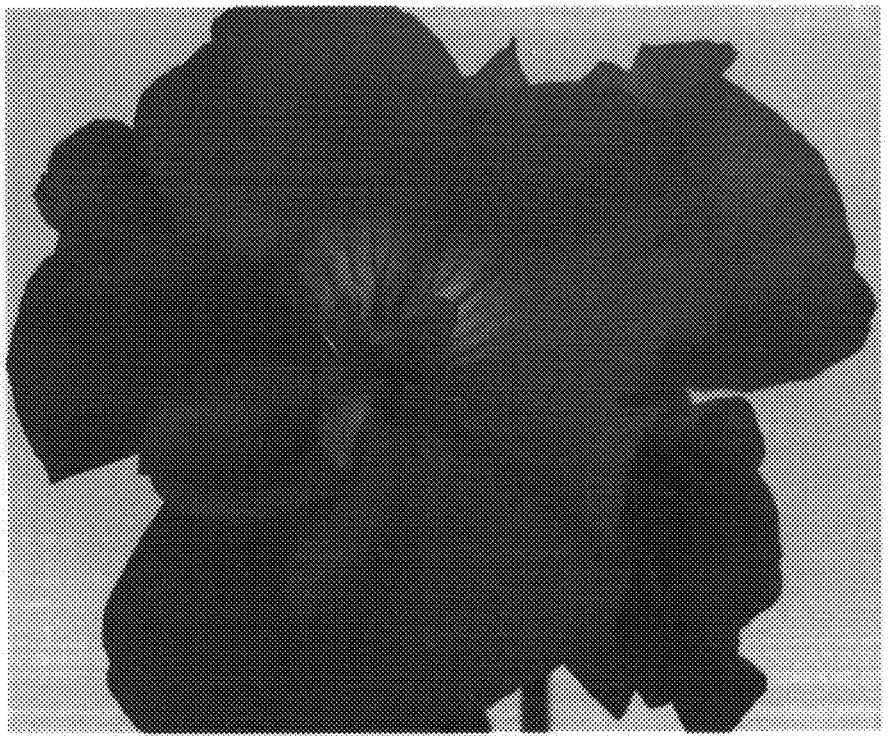

The photographic drawings show in FIG. 1, 3 flowering plants of the new variety and in FIG. 2, a close-up of an inflorescence.

DETAILED BOTANICAL DESCRIPTION

The plant descriptions, measurements, and photo were taken in Gilroy, Calif. in December 2017 under natural light. These plants were approximately 10 weeks old and were grown in 4.5 inch pots, in a greenhouse trial.

Color references are made to The Royal Horticultural Society Colour Chart (R.H.S.) 20015.

TABLE 1

DIFFERENCES BETWEEN THE NEW VARIETY 'PEQZ0046' AND A MOST SIMILAR VARIETY

| | 'PEQZ0046' | 'PEQZ0032' (U.S. Plant Pat. No. 29,524) |
|---|---|---|
| Floret petal color: | Hot rose with white showing in center of petal | Solid color all magenta |
| Umbel diameter size: | Smaller | Larger |
| Leaves: | Dark zonation | Much less zonation |

Plant:

*Form, growth and habit.*—Upright, outwardly spreading and rounded growth habit, heat and drought tolerant with continuous color through the most extreme summer heat, edema tolerance, well-branched plant habit.

*Plant height.*—15-17.0 cm.

*Plant height (inflorescence included).*—24-29.0 cm.

*Plant width.*—31-35.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B.

Foliage:

*Immature leaf, color upper surface.*—RHS 144A.

*Immature leaf, lower surface.*—RHS 144B.

*Mature leaf, color upper surface.*—RHS 137A.

*Mature leaf, color lower surface.*—RHS 137C.

*Variegation of the leaf blade.*—Absent but does have a dark leaf zone.

*Length.*—8-10.0 cm.

*Width.*—10-11.0 cm.

*Shape.*—Cordate to orbicular.

*Base shape.*—Cordate.

*Apex shape.*—Acute to apiculate.

*Margin.*—Dentate to ciliate.

*Texture upper side.*—Hirsute.

*Texture lower side.*—Hirsute.

*Leaf zonation color.*—None.

*Color of veins, upper surface.*—RHS 137C.

*Color of veins, lower surface.*—RHS 137D.

*Pattern of veining.*—Palmate.

*Petiole color.*—RHS 137D.

*Petiole length.*—7.5-9.0 cm.

*Diameter of petiole.*—0.2 cm.

*Texture.*—Pilose, hirsute, glandular hairs.

Stem:

*Quantity of branches.*—3.

*Color of stem.*—RHS 144B.

*Length of stem.*—8-10.0 cm.

*Diameter.*—0.6-0.8 cm.

*Length of internodes.*—2.5-3.0 cm.

*Texture.*—Sparsely hirsute, pilose, glandular hairs.

Peduncle:

*Color of peduncle.*—RHS 137D.

*Length of peduncle.*—13-19.0 cm.

*Peduncle diameter.*—0.35-0.4 cm.

*Texture.*—Hirsute, glandular hairs.

Pedicel:

*Color of pedicel.*—RHS 187B.

*Length of pedicel.*—2.8-3.2 cm.

*Diameter of pedicel.*—0.15-0.2 cm.

*Texture.*—Sparsely pilose, glandular hiars.

Bud (just before opening):

*Color.*—RHS 45B.

*Length.*—1.9 cm.

*Width.*—0.8 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—7, with 3 immature umbels and 4 mature.

*Fragrance.*—None.

*Umbel diameter.*—8-10.0 cm.

*Umbel depth.*—6-8.0 cm.

Corolla:

*Form.*—Single.

*Number of petals.*—5.

*Diameter of flower.*—5-5.5 cm.

*Depth of flower.*—2-2.5 cm.

*Color upper petals, upper surface.*—Closest to RHS N57B with RHS N57B veining.

*Color upper petals, lower surface.*—Closest to RHS N57C with RHS N57B veining.

*Length of upper petals.*—3.0 cm.

*Width of upper petals.*—2.5-3.0 cm.

*Color lower petals, upper surface.*—Closest to RHS N66A.

*Color lower petals, lower surface.*—Closest to RHS N66C.

*Length of lower petals.*—2.8 cm.

*Width of lower petals.*—2.6 cm.

*Petal shape.*—Obovate to orbicular.

*Apex shape.*—Rounded.

*Margin.*—Entire.

*Base.*—Attenuate to cordate.

*Petal texture.*—Papillose on both surfaces.

Calyx:

*Number of sepals.*—5.

*Color of sepals.*—RHS 144B.

*Length of sepals.*—1.1-1.3 cm.

*Width of sepals.*—0.3-0.4 cm.

*Sepal shape.*—Lanceolate to linear.

*Apex shape.*—Apiculate.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—0.8-1.0 cm.

*Style color.*—Closest to RHS 53C.

*Style length.*—0.3-0.4 cm.

*Stigma color.*—Closest to RHS 53C.

*Ovary color.*—RHS 144A.

*Ovary length.*—0.3-0.4 cm.

*Ovary diameter.*—0.2 cm.

Androecium:

*Number of stamens*.—7-9.

*Color of filaments*.—RHS 66B with RHS NN155D basally.

*Length filaments*.—0.8-1.0 cm.

*Anther color*.—RHS 25B.

*Length of anthers*.—0.2 cm.

*Color of pollen*.—RHS N25B.

*Pollen amount*.—Moderate.

*Fertility/seed set*.—Has not been determined to date.

*Disease/pest resistance*.—Has not been determined to date.

What is claimed is:

1. A new and distinct variety of *Pelargonium* plant named 'PEQZ0046' substantially as illustrated and described herein.

* * * * *